United States Patent [19]

Gehrmann et al.

[11] Patent Number: 4,518,538

[45] Date of Patent: May 21, 1985

[54] PROCESS FOR MAKING METHYLDICHLOROPHOSPHANE

[75] Inventors: Klaus Gehrmann; Alexander Ohorodnik, both of Erftstadt; Johannes Rosenthal, Cologne; Stefan Schäfer, Brühl, all of Fed. Rep. of Germany

[73] Assignee: Hoechst Aktiengesellschaft, Frankfurt, Fed. Rep. of Germany

[21] Appl. No.: 442,106

[22] Filed: Nov. 16, 1982

[30] Foreign Application Priority Data

Dec. 17, 1981 [DE] Fed. Rep. of Germany ....... 3149937

[51] Int. Cl.$^3$ .............................................. C07F 9/52
[52] U.S. Cl. ................................................ 260/543 P
[58] Field of Search ................................... 260/543 P

[56] References Cited

U.S. PATENT DOCUMENTS 4,101,573  7/1978  Gehrmann et al. ............ 260/543 P

Primary Examiner—Natalie Trousof
Assistant Examiner—L. Hendriksen
Attorney, Agent, or Firm—Connolly and Hutz

[57] ABSTRACT

The disclosure relates to a process for making methyldichlorophosphane by reacting methane with phosphorus trichloride in the presence of 2 to 7 mol % carbon tetrachloride, based on the phosphorus trichloride used, at temperatures of 500° to 650° C. and over a period of time of 0.1 to 0.9 second. More particularly, the reaction is effected under a pressure of 2 to 10 bars, the proportion of carbon tetrachloride added being reduced at increasing pressure.

1 Claim, No Drawings

PROCESS FOR MAKING METHYLDICHLOROPHOSPHANE

A process for making methyldichlorophosphane by reacting methane and phosphorus trichloride in the presence of 3 to 20 mol% carbon tetrachloride, based on the phosphorus trichloride used, at temperatures above 500° C., which comprises adding 2 to 7 mol% carbon tetrachloride based on the phosphorus trichloride, as an initiator to the feed mixture and reacting the carbon tetrachloride to an extent of 50 to 80% at constant reaction periods of 0.1 to 0.9 second by varying the reaction temperature between 500° and 650° C. has already been described in German Patent Specifications DE-PS Nos. 26 29 299 and 27 01 389.

As taught therein, the reaction which occurs in accordance with the following equation

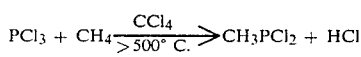
$$PCl_3 + CH_4 \xrightarrow[>500° C.]{CCl_4} CH_3PCl_2 + HCl$$

is effected at atmospheric pressure as the volue of the reactants remains unchanged under the conditions prevailing before and after reaction so that under kinetic aspects the pressure cannot reasonably be deemed to affect the course of the reaction. In other words, the use of elevated pressure for effecting this reaction would not have been expected to entail practical advantages.

In clear contrast with what could generally be deduced from the reaction kinetics, it has unexpectedly been found that the step of carrying out this reaction under elevated pressure in fact entails significant advantages. This unexpected result is theoretically attributable to the fact that it is necessary for the carbon tetrachloride-initiated chain reaction which results in the formation of methyldichlorphosphane to comprise at least one pressure-responsive partial step. In practice, the reaction of phosphorus trichloride with methane in the presence of carbon tetrachloride under elevated pressure on the one hand, results in the space/time-yield becoming considerably improved and, on the other hand, results in the quantity of carbon tetrachloride needed, based on the unit mass of methyldichlorophosphane to be made, being significantly reduced. At the high reaction temperatures selected, carbon tetrachloride undergoes reaction to various by-products such as vinyl chloride, 1,1-dichloroethylene, tetrachloroethylene and hexachloroethane, so that any reduction of the carbon tetrachloride content in the reaction mixture necessarily results in the quantity of these ecologically pollutive by-products being reduced so that they are less expensive to disposed of than heretofore.

The present invention relates more particularly to a process for making methyldichlorophosphane by reacting methane and phosphorus trichloride in the presence of 2 to 7 mol% carbon tetrachloride, based on the phosphorus trichloride used, at temperatures of 500° to 650° C. and over a period of time of 0.1 to 0.9 second, which comprises: effecting the reaction under a pressure of 2 to 10 bars, preferably 3 to 6 bars, the proportion of carbon tetrachloride being reduced at increasing pressure.

EXAMPLES 1 to 4

Gaseous mixtures containing $CH_4$ and $PCl_3$ in a molar ratio of 4:1 were introduced into a tubular stainless steel ("Hastelloy-C") reactor electrically heatable, 180 cm long, and with 778 $cm^3$ free reactor volume, allowed to remain therein over a constant period of 0.8 second at a constant temperature of 580° C. while varying the reaction pressure. the reaction mixture coming from the reactor was cooled stagewise to $-60°$ C., the resulting condensate was analyzed gas-chromatographically and the results obtained were evaluated. The test results critical for the evaluation of the present process (Examples 2 to 4) are indicated in the following Table.

| Ex. | Pressure bars | Space/time-yield* g MDP/l/h | CCl$_4$ needed g/kg MDP | Chlorine-containing by-products obtained g/kg MDP |
|---|---|---|---|---|
| 1 | 1.1 | 590 | 220 | 180 |
| 2 | 3.0 | 800· | 180 | 80 |
| 3 | 3.75 | 880 | 160 | 50 |
| 4 | 4.5 | 940 | 110 | 38 |

MDP = methyldichlorophosphane
*Space/time-yield: g MDP per 1 l reactor volume per hour It is also noteworthy that the increase in pressure could not be found to impair the yield. In each of Examples 1 to 4, the yield (selectivity) was about 98%, based on the phosphoros trichloride converted.

We claim:

1. In a process for making methyldichlorophosphane by reacting methane with phosphorus trichloride in the presence of 2 to 7 mol percent carbon tetrachloride, based on the phosphorus trichloride used, at temperatures of 500° to 650° C. and over a period of time of 0.1 to 0.9 second, the improvement which comprises effecting the reaction under a pressure of 3 to 6 bars, the proportion of carbon tetrachloride added being reduced at increasing pressure.

* * * * *